United States Patent

Hack et al.

[11] 4,123,253
[45] Oct. 31, 1978

[54] HERBICIDAL COMPOSITIONS

[75] Inventors: Helmut Hack, Odenthal; Robert R. Schmidt, Cologne; Karlfried Dickoré, Leverkusen, all of Germany

[73] Assignee: Bayer Aktiengesellschaft, Leverkusen, Germany

[21] Appl. No.: 722,305

[22] Filed: Sep. 10, 1976

[30] Foreign Application Priority Data

Oct. 2, 1975 [DE] Fed. Rep. of Germany ....... 2543974

[51] Int. Cl.² .................... A01N 9/22; A01N 9/02
[52] U.S. Cl. .......................... 71/93; 71/108; 71/109; 71/110; 71/116; 71/117
[58] Field of Search ............................ 71/93

[56] References Cited
U.S. PATENT DOCUMENTS 3,628,943  12/1971  Gullfeldt .................... 71/93
3,671,523  6/1972   Westphal et al. ............ 71/93

FOREIGN PATENT DOCUMENTS 416,598  4/1963  Japan ..................... 71/93

Primary Examiner—Catherine L. Mills
Attorney, Agent, or Firm—Burgess, Dinklage & Sprung

[57] ABSTRACT

The invention provides herbicidal compositions containing as active ingredients (1) a 1,2,4-triazin-5-(4H)-one derivative of the general formula

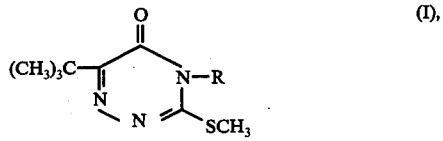

(I), in which
R is amino or isobutylideneamino, and (2) a phenoxyalkanecarboxylic acid of the general formula

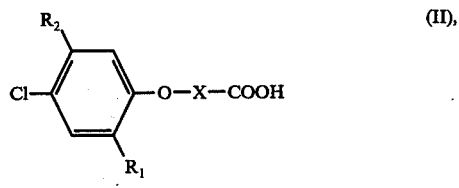

(II), in which
X is methylene or methylmethylene,
$R_1$ is chlorine or methyl and
$R_2$ is hydrogen or chlorine,
which may be in the form of a salt or ester thereof, alone or in admixture with a solid or liquid or liquefied gaseous diluent or carrier;

which combinations provide synergistic weed-killing action against a wide range of weeds in cereals.

16 Claims, No Drawings

HERBICIDAL COMPOSITIONS

The present invention relates to new herbicidal synergistic combinations of certain 1,2,4-triazin-5(4H)-one derivatives and certain phenoxyalkanecarboxylic acids.

It is known that 6-tert.-butyl-4-amino- and 6-tert.-butyl-4-isobutylideneamino-3-methylthio-1,2,4-triazin-5(4H)-one can be used as selective herbicides, from U.S. Pat. No. 3,671,523. Further, it is known that phenoxyalkanecarboxylic acids can be used as herbicides in cereals, from U.S. Pat. No. 2,740,810 and British patent specification No. 822,199. However, with both types of preparations the herbicidal activity is not always satisfactory for combating weeds in cereals, if low amounts and low concentrations are used, especially where weeds and wild grasses which are difficult to combat are concerned.

Thus, the action of the said 1,2,4-triazinone derivatives against cleavers (*Galium aparine*) and chamomile (*Matricaria sp.*) is inadequate even if fairly high amounts are used. the phenoxyalkanecarboxylic acids are inactive against meadow foxtail grass (*Alopecurus myosuroides*), silky bent-grass (*Apera spica-venti*) and annual bluegrass (*Poa annua*).

The present invention provides a herbicidal composition containing as active ingredients (1) a 1,2,4-triazin-5-(4H)-one derivative of the general formula

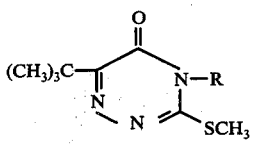

in which
R is amino or isobutylideneamino, and (2) a phenoxyalkanecarboxylic acid of the general formula

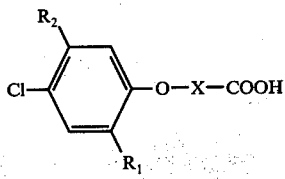

in which
X is methylene or methylmethylene,
$R_1$ is chlorine or methyl and
$R_2$ is hydrogen or chlorine,
which may be in the form of a salt or ester thereof, alone or in admixture with a solid or liquid or liquefied gaseous diluent or carrier.

Surprisingly, the activity of the active-compound combinations according to the invention is substantially higher than the sum of actions of the individual active compounds. An unforeseeable genuine synergistic effect is concerned, and not merely a supplementary action. This synergistic effect manifests itself particularly strongly at certain concentration ratios.

The present compositions exhibit a particularly good herbicidal action for the selective combating of a wide range of weeds in cereals.

The present invention also provides a method for combating weeds, which comprises applying to the weeds or to a weed habitat, a composition of the present invention.

The active-compound combinations according to the invention offer the advantage, over the individual active compounds known from the state of the art, that the weeds and wild grasses which are otherwise very difficult to combat can be combated simultaneously, by using the active compound combination according to the invention at only one point in time, without damaging the cereal culture. The active compound combinations according to the invention thus represent a valuable enrichment of cereal herbicides.

Other weeds commonly occur in cereal cultures are also combated reliably by the active-compound combinations according to the invention. Examples of such weeds are species of Stellaria, Veronica, Lamium, Papaver and Polygonum.

The forumla (I) comprises two active compounds, 6-tert.-butyl-3-methylthio-4-amino-1,2,4-triazin-5-(4H)-one (Ia) and 6-tert.-butyl-4-isobutylideneamino-3-methylthio-1,2,4-triazin-5(4H)-one (Ib); these are already known (see U.S. Pat. No. 3,671,523).

Particularly preferred phenoxyalkanecarboxylic acids of the formula (II) ar 2,4-dichlorophenoxyacetic acid (2,4-D) (IIa), α-(2,4-dichlorophenoxy)-propionic acid (2,4-DP) (IIb), 2-methyl-4-chlorophenoxyacetic acid (MCPA) (IIc) and α-(2-methyl-4-chlorophenoxy)-propionic acid (MCPP) (IId).

The phenoxycarboxylic acids of the formula (II) can be present in the active compound combinations as such, in the form of the metal salts, especially the alkali metal salts, in the form of the ammonium salt or of the amine salts, and in the form of the esters.

The weight ratios of the active compounds (1) and (2) in the active-compound combinations can be varied within a relatively wide range. In general, 1 to 10 parts by weight of active compound (2), preferably 2 to 10 parts by weight, are present per part by weight of active compound (1).

The active-compound combinations according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulfoxide or acetonitrile, as well as water.

By liquefied gaseous diluents or carriers are meant liquids which could be gaseous at normal temperatures and pressures, for example aerosol propellants, such as halogenated hydrocarbons, for example freon.

As solid diluents or carriers, there are preferably used ground natural minerals, such as kaolins, clays, talc, chalk, quartz, attapulgite, montmorillonite or diatomaceous earth, or ground synthetic minerals, such as highly dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulfonates, alkyl sulfates and aryl sulfonates as well as albumin hydrolyzation products; and preferred examples of dispersing agents include lignin sulfite waste liquors and methyl cellulose.

The active-compound combinations according to the invention can be present in the formulations together with other known active compounds. The formulations in general contain from 0.1 to 95 percent by weight of active compound combinations, preferably from 0.5 to 90 percent by weight.

The active-compound combinations can be used as such, in the form of their formulations or as the use forms prepared therefrom, such as ready-to-use solutions, emulsions, suspensions, powders, pastes and granules. They may be used in the customary manner, for example by dusting, atomizing, spraying, watering and scattering.

The amounts used of the active-compound combinations according to the invention can be varied within a fairly wide range. In general, the amounts used are between 1 and 10 kg/ha, preferably between 1 and 5 kg/ha.

Preferably, the active-compound combinations according to the invention are used after the emergence of the plants.

The present invention also provides crops protected from damage by weeds by being grown in areas in which immediately prior to and/or during the time of the growing a composition of the present invention was applied.

The good herbicidal action of the active-compound combinations can be seen from the examples which follow. While the individual active compounds show weaknesses in their herbicidal action, the combinations exhibit a very broad action against weeds and wild grasses, which goes beyond a simple summation of their actions.

A synergistic effect exists, with herbicides, whenever the herbicidal action of the active compound combination is greater than that of the individually applied active compounds.

The action to be expected for a given combination of two herbicides can be calculated as follows (see Colby, S.R., "Calculating synergistic and antagonistic response of herbicide combinations," Weeds 15, pages 20–22, 1967):

if $X$ = % damage by herbicide A using $p$ kg/ha, and
$Y$ = % damage by herbicide B using $q$ ka/ha, and
$E$ = the expected damage by herbicides A and B using $p+q$ ka/ha,
then $E = X + Y - (X \cdot Y/100)$ If the actual damage is greater than calculated, the action of the combination is super-additive, that is to say a synergistic effect is concerned.

The tables of Example A and B show unambiguously that the found herbicidal action of the active-compound combinations according to the invention on weeds is greater than that calculated, that is to say a genuine synergistic effect is concerned.

The specific active compounds are identified by the numbers assigned to them in the list which follows Example B.

EXAMPLE A

Field experiments/winter barley

Post-emergence test/open ground/wettable powder
Inert carrier material: 0.25 part by weight of kaolin and silica (3:1)
Protective colloid: 0.02 part by weight of lignin sulfate
Dispersing auxiliary: 0.15 part by weight of hydroxyarylsulfonic acid/formaldehyde condensate To produce a suitable preparation of active compound, 1 part by weight of active compound was mixed with the stated amounts of formulation auxiliaries and the concentrate was subsequently diluted with water to the desired concentration.

In open ground, plots of test plants which were about 10–20 cm high were sprayed with an amount of active compound preparation such as to give uniform wetting of the plants. The deciding factor was the amount of active compound used per unit surface area. After 3 weeks, the degree of damage of the plants was assessed in % damage in comparison to the untreated control.

The figures denote:

0% = untreated control/no action
100% = total destruction

The active compounds, amounts used and results can be seen from the table which follows:

Table A

| Active compound or active compound combination | Amount of active compound used. kg/hg | Alopecurus myosuroides | | Galium aparine | | Matricaria chamomilla | | Veronica Hederifolia | | Winter barley |
|---|---|---|---|---|---|---|---|---|---|---|
| | | found | calc. | found | calc. | found | calc. | found | calc. | |
| (Ib) | 0.7 | 88 | | 10 | | 70 | | 80 | | 0 |
| (known) | 0.9 | 95 | | 15 | | 75 | | 95 | | 0 |
| | 1.0 | 100 | | 20 | | 80 | | 100 | | 0 |
| (IIb) | 1.6 | 0 | | 85 | | 80 | | 40 | | 0 |
| (known) | 1.8 | 0 | | 92 | | 90 | | 50 | | 0 |
| Combination | 0.9 + 1.8 | 98 | 95 | 98 | 93.2 | 100 | 97.5 | 100 | 97.5 | 0 |
| (Ib) + (IIb) | 0.7 + 1.6 | 92 | 88 | 92 | 86.5 | 100 | 94 | 95 | 88 | 0 |
| | 1.0 + 1.8 | 100 | 100 | 100 | 93.6 | 100 | 98 | 100 | 100 | 0 | found = damage found
calc. = damage calculated according to the equation given earlier

EXAMPLE B

Field experiments/summer barley

Post-emergence test/open ground/wettable powder
Inert carrier material: 0.25 parts by weight of kaolin and silica (3:1)

Protective colloid: 0.02 parts by weight of lignin sulfate
Dispersing auxiliary: 0.15 part by weight of hydroxyarylsulfonic acid/formaldehyde condensate To produce a suitable preparation of active compound, 1 part by weight of active compound was mixed with the stated amount of formulation auxiliaries and the concentrate was subsequently diluted with water to the desired concentration.

In open ground, plots of test plants which were about 3–10 cm high were sprayed with an amount of active compound preparation such as to give uniform wetting of the plants. The deciding factor was the amount of active compound used per unit surface area. After 3 weeks, the degree of damage of the plants was assessed in % damage in comparison to the untreated control.

The figures denote:
0% = untreated control/no action
100% = total destruction.

The active compounds, amounts used and results can be seen from the table which follows:

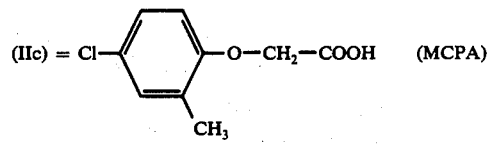
(MCPA)
(formulated as the sodium salt)

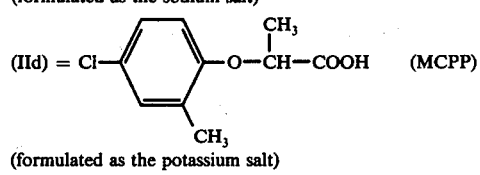
(MCPP)
(formulated as the potassium salt)

It will be understood that the specification and examples are illustrative but not limitative of the present invention and that other embodiments within the spirit and scope of the invention will suggest themselves to those skilled in the art.

Table B

Post-emergence test/open ground, summer barley
Percentage damage of weeds and wild grasses in field experiments
Mean values from four repeats

| Active compound or active compound combination | Amount of active compound used, kg/hg | Apera spica-venti | | Polygonum aviculare | | Galium aparine | | Summer barley | |
|---|---|---|---|---|---|---|---|---|---|
| | | found | calc. | found | calc. | found | calc. | found | calc. |
| (Ib) | 0.3 | 90 | | 40 | | 0 | | 0 | |
| (known) | 0.4 | 95 | | 60 | | 0 | | 0 | |
| | 0.6 | 100 | | 90 | | 10 | | 0 | |
| (IIb) | 1.2 | 0 | | 90 | | 70 | | 0 | |
| (known) | 1.5 | 0 | | 100 | | 95 | | 0 | |
| (IId) | 1.2 | 0 | | 80 | | 75 | | 0 | |
| (known) | 1.5 | 0 | | 90 | | 95 | | 0 | |
| (Ib + IIb) | 0.3 + 1.5 | 95 | 90 | 100 | 100 | 98 | 95 | 0 | |
| according to the | 0.4 + 1.2 | 98 | 95 | 99 | 96 | 80 | 70 | 0 | |
| invention | 0.6 + 1.2 | 100 | 100 | 99 | 99 | 85 | 73 | 0 | |
| (Ia + IId) | 0.3 + 1.5 | 96 | 90 | 100 | 94 | 100 | 95 | 0 | |
| according to the | 0.4 + 1.2 | 98 | 95 | 98 | 92 | 85 | 75 | 0 | |
| invention | 0.6 + 1.2 | 100 | 100 | 100 | 98 | 88 | 77.5 | 0 | | found = damage found
calc. = damage calculated according to the equatin given earlier List of active compounds

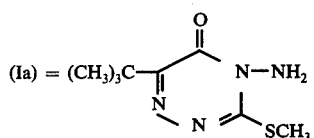

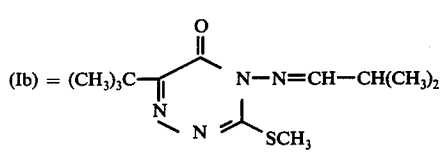

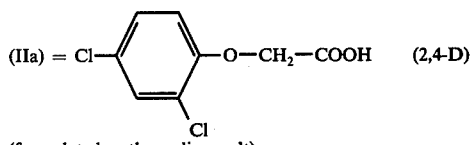
(2,4-D)
(formulated as the sodium salt)

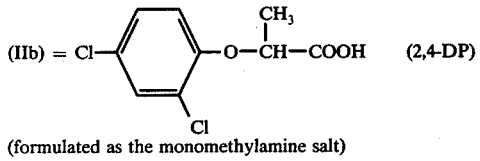
(2,4-DP)
(formulated as the monomethylamine salt)

What is claimed is:
1. Herbicidal composition for the selective combating of weeds in cereal cultures, containing as active ingredients (1) a 1,2,4-triazin-5(4H)-one derivative of the general formula

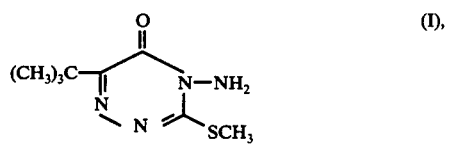
(I), and (2) a phenoxyalkanecarboxylic acid of the general formula

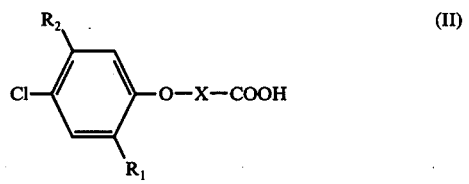
(II)

in which
X is methylene or methylmethylene,
$R_1$ is chlorine or methyl and
$R_2$ is hydrogen or chlorine, which acid may be in the form of a salt or ester thereof, the weight ratio of (1) to (2) being about 1:2-5.

2. Herbicidal composition as claimed in claim 1 wherein X in formula II is methylene.

3. Herbicidal composition as claimed in claim 1 wherein X in formula II is methylmethylene.

4. Herbicidal composition as claimed in claim 1 wherein $R_1$ in formula II is chlorine.

5. Herbicidal composition as claimed in claim 1 wherein $R_1$ in formula II is methyl.

6. Herbicidal composition as claimed in claim 1 wherein $R_2$ in formula II is hydrogen.

7. Herbicidal composition as claimed in claim 1 wherein $R_2$ in formula II is chlorine.

8. Herbicidal composition as claimed in claim 1 wherein the phenoxyalkanecarboxylic acid is of the formula:

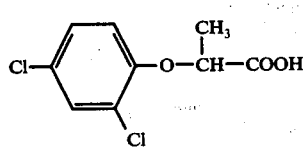
(IIb)

9. Herbicidal composition as claimed in claim 1 wherein the phenoxyalkanecarboxylic acid is of the formula:

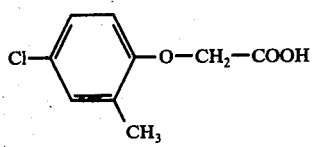
(IIc)

10. Herbicidal composition as claimed in claim 1 wherein the phenoxyalkanecarboxylic acid is of the formula:

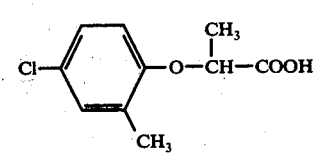
(IId)

11. Herbicidal composition as claimed in claim 1 wherein the phenoxyalkanecarboxylic acid is employed in the form of an alkali metal, ammonium or amine salt thereof.

12. Herbicidal composition as claimed in claim 1 containing from 0.1 to 95% of total active compounds, by weight.

13. Method for combatting undesired vegetation which method comprises applying to such vegetation or its habitat a herbicidal composition as claimed in claim 1.

14. Method as claimed in claim 13 wherein the active ingredients are applied to an area of agriculture in a total amount of between 1 and 10 kg/hectare.

15. Method as claimed in claim 14 wherein the compounds are applied to an area of agriculture in a total amount of between 1 and 5 kg/hectare.

16. Method as claimed in claim 13 wherein the compounds are applied to an area of cereal cultivation.

* * * * *